(12) United States Patent
Basu et al.

(10) Patent No.: US 9,150,434 B2
(45) Date of Patent: Oct. 6, 2015

(54) ELECTRICITY-LESS WATER DISINFECTION

(71) Applicant: International Business Machines Corporation, Armonk, NY (US)

(72) Inventors: Anirban Basu, Elmsford, NY (US); Stephen W. Bedell, Wappingers Falls, NY (US); Devendra K. Sadana, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/673,520

(22) Filed: Nov. 9, 2012

(65) Prior Publication Data

US 2014/0131287 A1 May 15, 2014

(51) Int. Cl.
*C02F 1/32* (2006.01)
*A61L 2/00* (2006.01)
*A61L 9/00* (2006.01)

(52) U.S. Cl.
CPC . *C02F 1/325* (2013.01); *A61L 2/00* (2013.01); *A61L 9/00* (2013.01); *C02F 2201/009* (2013.01); *C02F 2201/3222* (2013.01); *C02F 2201/3227* (2013.01); *C02F 2303/04* (2013.01); *C02F 2307/02* (2013.01); *C02F 2307/04* (2013.01)

(58) Field of Classification Search
USPC ........... 210/739, 748.01, 748.11, 87, 91, 105, 210/192, 242.1, 295, 799; 422/24, 186, 422/186.3, 400; 136/243, 244, 252, 261
See application file for complete search history.

(56) References Cited

U.S. PATENT DOCUMENTS

| | | | |
|---|---|---|---|
| 4,438,337 A | 3/1984 | Forrat | |
| 4,740,431 A | 4/1988 | Little | |
| 5,013,417 A | 5/1991 | Judd, Jr. | |
| 6,299,770 B1 | 10/2001 | Diener et al. | |
| 8,507,941 B2 * | 8/2013 | Khan et al. ....................... | 257/99 |

(Continued)

FOREIGN PATENT DOCUMENTS

| | | |
|---|---|---|
| WO | WO 2008033016 | 3/2008 |
| WO | WO 2009-108045 A1 | 9/2009 |

OTHER PUBLICATIONS

Daniel Mausezah et al., "Solar Drinking Water Disinfection (SODIS) to Reduce Childhood Diarrhoea in Rural Bolivia: A Cluster-Randomized, Controlled Trial", 2009.

(Continued)

*Primary Examiner* — Walter D Griffin
*Assistant Examiner* — Cameron J Allen
(74) *Attorney, Agent, or Firm* — Louis Percello

(57) ABSTRACT

Disinfecting a sample of water includes generating a current using an array of photovoltaic cells, using the current to power an array of light emitting diodes, wherein the array of light emitting diodes emits a germicidal wavelength of radiation, and exposing the sample of water to the radiation. Another method for disinfecting a sample of water includes placing the sample of water within a container, wherein the container includes an array of photovoltaic cells encircling an exterior wall of the container and an array of light emitting diodes encircling an interior wall of the container, placing the container in a location exposed to solar radiation, converting the solar radiation to a current using the array of photovoltaic cells, and powering the array of light emitting diodes using the current, wherein the array of light emitting diodes emits a germicidal wavelength of radiation sufficient to disinfect the sample of water.

20 Claims, 3 Drawing Sheets

(56) References Cited

U.S. PATENT DOCUMENTS

| | | |
|---|---|---|
| 2005/0242013 A1 | 11/2005 | Hunter et al. |
| 2005/0258108 A1* | 11/2005 | Sanford .................. 210/748 |
| 2006/0131246 A1 | 6/2006 | Ehlers |
| 2006/0131511 A1* | 6/2006 | Ehlers .................... 250/373 |
| 2006/0163126 A1 | 7/2006 | Maiden |
| 2007/0003430 A1 | 1/2007 | Kaiser et al. |
| 2007/0181508 A1* | 8/2007 | Gui et al. ................ 210/748 |
| 2008/0035581 A1 | 2/2008 | Kuhlmann et al. |
| 2009/0084734 A1 | 4/2009 | Yencho et al. |
| 2010/0155339 A1 | 6/2010 | Gunter et al. |
| 2010/0311250 A1 | 12/2010 | Bedell et al. |
| 2011/0210268 A1 | 9/2011 | Dornseifer et al. |
| 2011/0214709 A1* | 9/2011 | Evelsizer et al. ............ 136/244 |

OTHER PUBLICATIONS

Yoon, et al., "Ultrathin Silicon Solar Microcells for Semitransparent, Mechanically Flexible and Microconcentrator Module Designs". Nature Materials, vol. 7. Nov. 2008.

* cited by examiner

ELECTRICITY-LESS WATER DISINFECTION

FIELD OF THE DISCLOSURE

The present disclosure relates generally to water disinfection and relates more specifically to electricity-less water disinfection systems.

BACKGROUND OF THE DISCLOSURE

Recent studies by the World Health Organization indicate that as many as one billion people lack access to a source of improved drinking water. Consequently, more than two million people die per year of waterborne disease, and more still are afflicted with non-fatal waterborne diseases. Most of these people live in developing countries, refugee camps, or disaster relief shelters, where conventional water treatment systems may be cost-prohibitive (or the resources required to power such systems—e.g., electricity, fuel, etc.—may not be readily available).

Conventional approaches to electricity-less water disinfection include of ultraviolet (UV) germicidal irradiation, which typically uses a mercury vapor lamp to deliver germicidal UV radiation. Although such systems compare favorably with other water disinfection systems, they also introduce environmental hazards that other systems do not. For instance, a full-spectrum mercury vapor lamp will produce ozone at certain wavelengths. Moreover, exposure to germicidal wavelengths of UV radiation can be harmful to humans (e.g., resulting in sunburn, skin cancer, or vision impairment).

SUMMARY OF THE DISCLOSURE

Disinfecting a sample of water includes generating a current using an array of photovoltaic cells, using the current to power an array of light emitting diodes, wherein the array of light emitting diodes emits a germicidal wavelength of radiation, and exposing the sample of water to the radiation.

Another method for disinfecting a sample of water includes placing the sample of water within a container, wherein the container includes an array of photovoltaic cells encircling an exterior wall of the container and an array of light emitting diodes encircling an interior wall of the container, placing the container in a location exposed to solar radiation, converting the solar radiation to a current using the array of photovoltaic cells, and powering the array of light emitting diodes using the current, wherein the array, of light emitting diodes emits a germicidal wavelength of radiation sufficient to disinfect the sample of water.

Yet another method for disinfecting a sample of water includes converting solar radiation into an electrical current, using the electrical current to power a source of a germicidal wavelength of radiation, and exposing the sample of water to the germicidal wavelength of radiation until a desired percentage of microorganisms in the sample of water is sterilized.

BRIEF DESCRIPTION OF THE DRAWINGS

The teachings of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

In one embodiment, the present invention is a method and apparatus for electricity-less water disinfection. Within the context of the present invention, "electricity-less" is understood to refer to the absence of a conventional infrastructure for delivering electricity (e.g., a power distribution grid). However, as will become apparent, embodiments of the present invention employ mechanisms for converting renewable sources of energy into direct current electricity. In particular, embodiments of the present invention disinfect water using an array of light emitting diodes (LEDs) powered by photovoltaic cells, thereby obviating the need for a conventional source of electricity. The water is efficiently and effectively disinfected using a system that is more compact, consumes less power, and is safer environmentally than conventional disinfection systems.

Figures 1A, 1B:
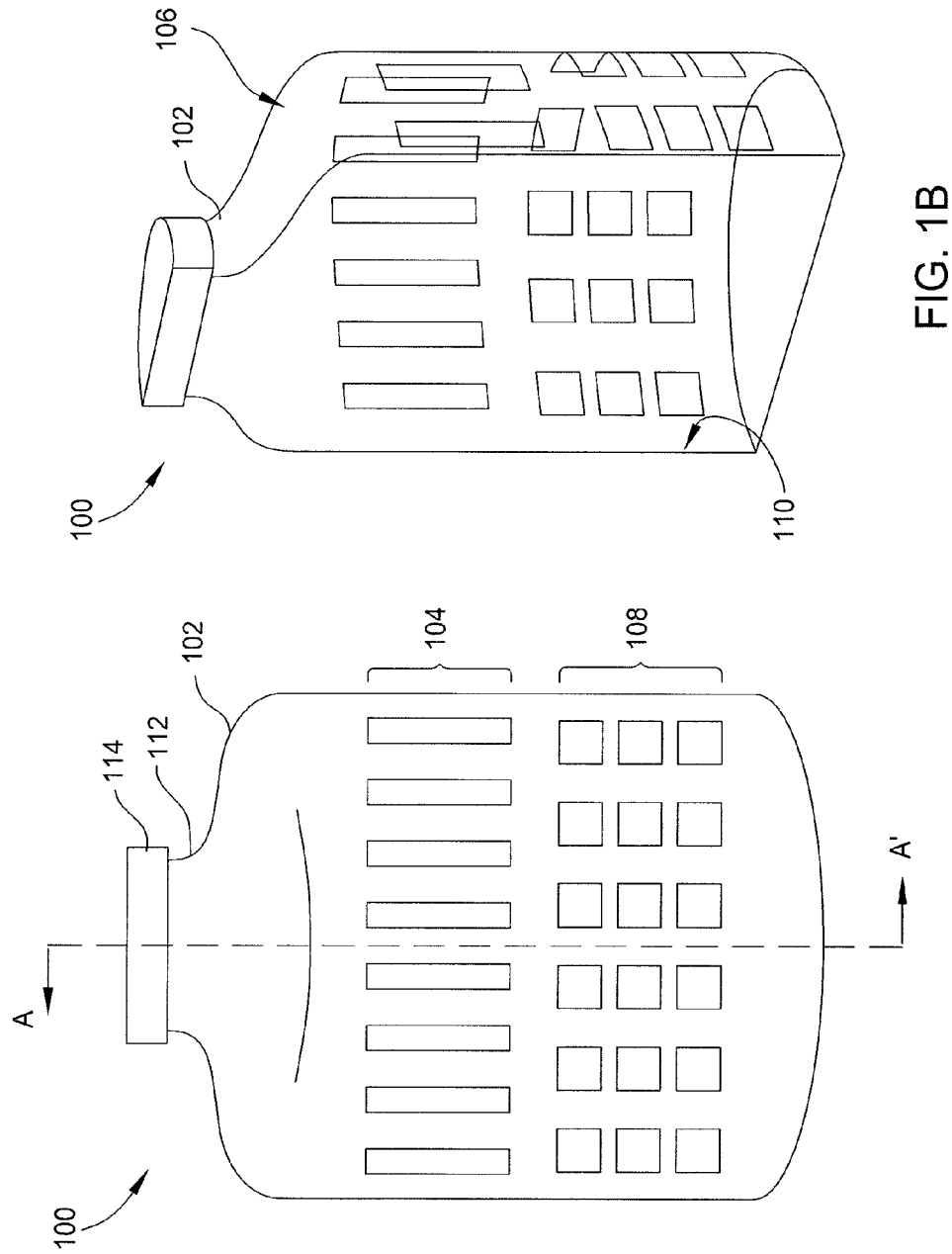
FIG. 1A is a plan view illustrating one embodiment of a water disinfection system, according to the present invention.
FIG. 1B is a cross-sectional view of the water disinfection system illustrated in FIG. 1A, taken along line A-A' of FIG. 1A.

FIG. 1A is a plan view illustrating one embodiment of a water disinfection system 100, according to the present invention. FIG. 1B is a cross-sectional view of the water disinfection system 100 illustrated in FIG. 1A, taken along line A-A' of FIG. 1A. The water disinfection system 100 employs a chemical-free process that directly attacks the vital deoxyribonucleic acid (DNA) of microorganisms (e.g., bacteria, mold, yeast, viruses, protozoa, etc.) in a water sample, thereby sterilizing the microorganisms and rendering the water sample suitable for human consumption.

Referring simultaneously to FIGS. 1A-1B, the system 100 generally comprises a rigid container 102, such as a jug or a bottle. The container 102 includes a neck 112 or other opening that allows water to be poured into the container 102 and a lid or cap 114 that seals the neck 112 (and thus the container 102). The container 102 thus defines a volume within which a quantity of water can be contained and disinfected according to the embodiments described below. In one embodiment, the container 102 holds up to approximately five gallons of liquid, although the container 102 can be manufactured in any size. In one embodiment, the container 102 is formed from a material that is known to be environmentally and health-safe (i.e., does not cause any significant negative environmental or health-related side effects), such as a Bisphenol A (BPA)-free polymer or plastic.

The system 100 further comprises an array 104 of photovoltaic cells (i.e., semiconductors that convert solar radiation to direct current electricity) coupled to the exterior wall 106 of the container 102. In one embodiment, the array 104 of photovoltaic cells encircles an entire perimeter of the exterior wall 106. In one embodiment, the array 104 comprises a plurality of micro-photovoltaic cells (e.g., photovoltaic cells having a size between approximately ten and one hundred micron). In a further embodiment, the photovoltaic cells are spalled (i.e., thin-film), flexible photovoltaic cells. In one embodiment, one or more of the photovoltaic cells is formed from at least one of: amorphous silicon, crystalline silicon, silicon germanium (SiGe), germanium (Ge), indium gallium arsenide (InGaAs), or indium arsenide (InAs).

In addition, an array 108 of LEDs is coupled to the interior wall 110 of the container 102. In one embodiment, the array 108 of LEDs encircles an entire perimeter of the interior wall 110. The array 108 of LEDs is also connected (e.g., by a system of interconnects) to the array 104 of photovoltaic cells such that current can pass from the photovoltaic cells to the LEDs. In one embodiment, the array 108 comprises a plurality of micro-LEDs (e.g., LEDs having dimensions less than or equal to one hundred micrometers×one hundred micrometers). In a further embodiment, the LEDs are spalled, flexible micro-LEDs arranged on a substrate (e.g., a silicon substrate) and coupled via a system of interconnects. In one embodiment, the micro LEDs are formed from aluminum gallium nitride (AlGaN) and/or gallium nitride (GaN). In one embodiment, each of the LEDs has a power output of approximately one milliwatt. The system 100 has been demonstrated to be capable of sterilizing up to at least ninety-nine percent of many different types of microorganisms in water. Water that has been sterilized to this degree would generally be considered potable.

Figure 2:
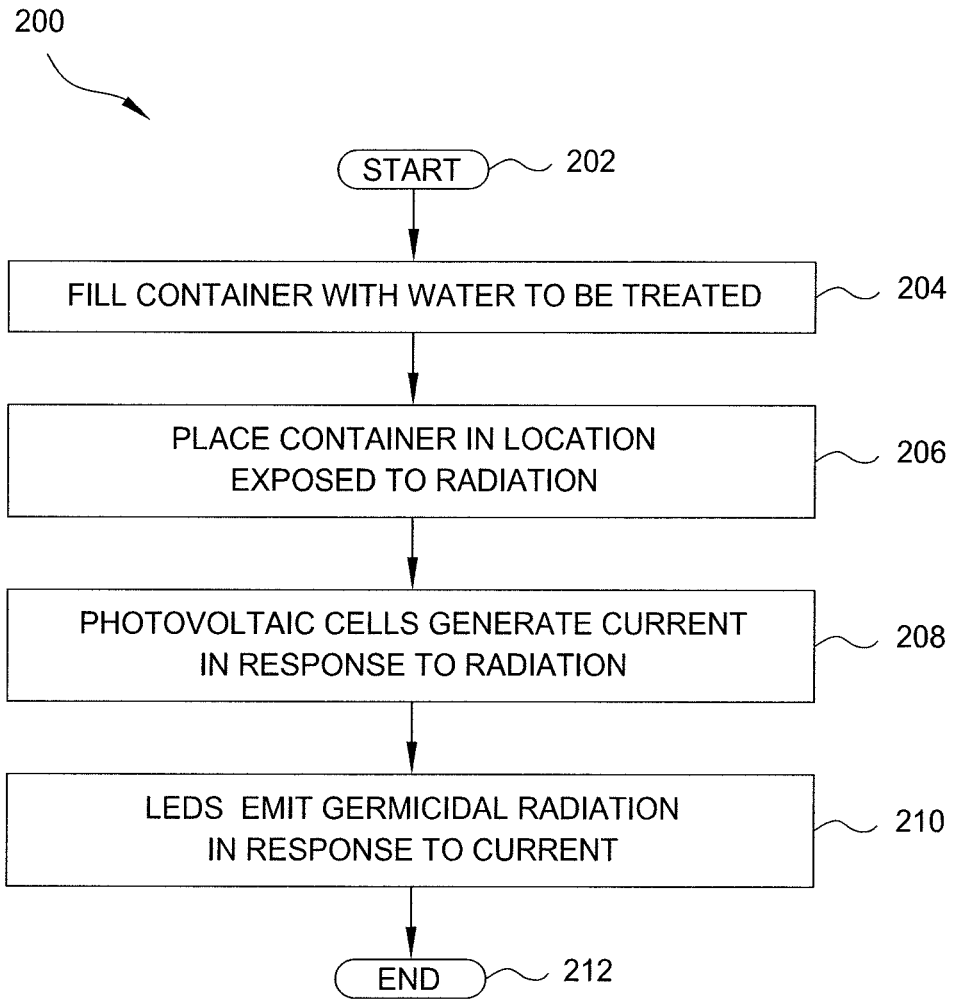
FIG. 2 is a flow diagram illustrating one embodiment of a method for disinfecting water, according to the present invention.

FIG. 2 is a flow diagram illustrating one embodiment of a method 200 for disinfecting water, according to the present invention. In particular, FIG. 2 illustrates how water may be disinfected using the water disinfection system 100 illustrated in FIGS. 1A-1B. As such, reference is made in the discussion of the method 200 to various items illustrated in FIGS. 1A-1B.

The method begins in step 202. In step 204, the container 102 is filled with a quantity of water to be treated. The container 102, including the water, is then placed in a location where it will be exposed to radiation (e.g., sunlight) in step 206.

In step 208, the array 104 of photovoltaic cells generates a current in response to the radiation. In one embodiment, the current generated by the array 104 of photovoltaic cells is in the milliwatt range.

In step 210, the array 108 of LEDs is activated and emits germicidal radiation in response to the current provided by the array 104 of photovoltaic cells. In one embodiment, the germicidal radiation is UV radiation (e.g., having a wavelength in the range of approximately 265 to 280 nanometers). Prolonged exposure to this germicidal radiation results in the sterilization of microorganisms in the water that is held within the container 102. As a result, the water is disinfected and rendered suitable for human consumption. In one embodiment, the length of time for which the water must be exposed to the germicidal radiation depends at least on the amount of water to be treated, the desired percentage and type of microorganisms to be sterilized, and the intensity of the germicidal radiation emitted by the array 108 of LEDs. For instance, in one embodiment, the water is exposed to the germicidal radiation for at least one minute; in further embodiments, the water is exposed to the germicidal radiation for up to an hour. Disinfection of the water is thus a product of the intensity of the germicidal radiation emitted by the array 108 of LEDs over the time of exposure and within the given area (i.e., the volume of the container 102). This exposure may be expressed in microwatt seconds per square centimeter.

The method 200 ends in step 212.

The method 200 thus employs a physical, chemical-free process that effectively and efficiently disinfects water without consuming electricity or causing any significant environmental side effects. Because the system 100 is compact and does not require electricity or fuel other than sunlight, it can be used in substantially any environment.

Moreover, the system 100 is cost effective to manufacture and to use. In particular, certain techniques, such as spalling, may be used to manufacture the system 100 in a manner that minimizes waste of materials or energy.

Figure 3:
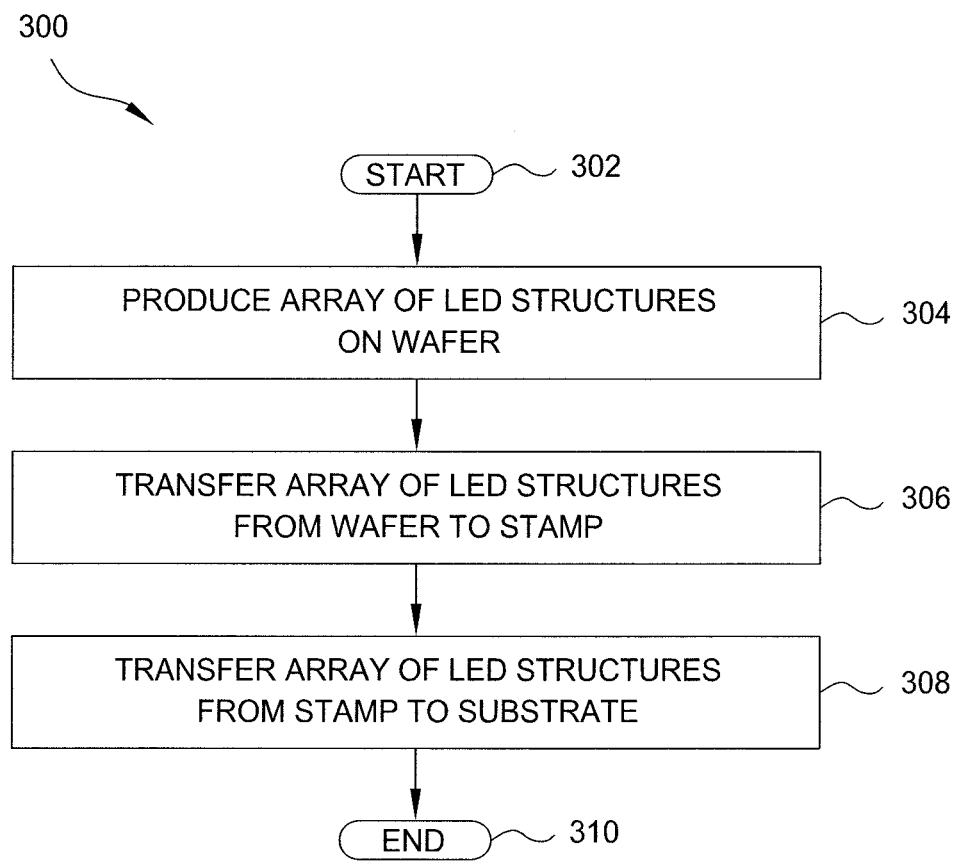
FIG. 3 is a flow diagram illustrating one embodiment of a method for manufacturing the water disinfection system illustrated in FIGS. 1A-1B.

FIG. 3 is a flow diagram illustrating one embodiment of a method 300 for manufacturing the water disinfection system 100 illustrated in FIGS. 1A-1B. In particular, the method 300 is one embodiment of a method for producing the array 108 of LEDs on the interior wall 110 of the container 102. The particular method 300 illustrated in FIG. 3 relies on a spalling technique to produce the LED array 108.

The method 300 begins in step 302. In step 304, an array of LED structures is produced on a wafer (e.g., a silicon substrate). The array of LED structures may be produced using any one or more known manufacturing techniques. For instance, a stack of layers comprising a silicon substrate, an aluminum nitride layer formed on the silicon substrate, and a gallium nitride layer formed on the aluminum nitride layer can be fabricated. The stack may additionally comprise a plurality of contacts (e.g., p- and n-type contacts). Dry etching of the aluminum nitride and gallium nitride layers can expose the silicon substrate, which may then be anisotropically etched using potassium hydroxide (KOH), leaving an array of anchored gallium nitride/aluminum nitride structures.

In step 306, the array of LED structures is transferred from the wafer to a stamp. For instance, a patterned polydimethylsiloxane (PDMS) stamp may be brought into contact with the wafer and then quickly removed, causing chips of gallium nitride/aluminum nitride to be released from the wafer and adhered to the stamp as a plurality of discrete thin film devices. This technique may also be referred to as "spalling."

In step 308, the array of LED structures is transferred from the stamp to a substrate. For instance, the stamp may be brought into contact with the substrate and then slowly removed, causing the array of LED structures to adhere to the substrate as a plurality of discrete thin film devices (i.e., the array of LEDs). This may be accomplished using a transfer printing technique. In one embodiment, the substrate already includes a layer of interconnects (and adhesive) onto which the thin film devices are deposited. An additional layer of interconnects may then be deposited on the thin film devices (e.g., after planarization of the thin film devices). As a result, a printed array of micro LEDs is fabricated upon the substrate. In one embodiment, the substrate is or will become the inner surface 110 of the container 102. Thus, in one embodiment, the substrate is a BPA-free polymer.

The method 300 ends in step 310.

The method 300 thus results in the application of an array 108 of thin-film LEDs to the inner surface 110 of the container 102. As discussed above, spalling can also be used to apply the array 104 of photovoltaic cells to the outer surface 106 of the container 102. This technique allows a dense array to be distributed on a sparse array, thereby making economical use of materials by reducing the cost and area of material used.

Although various embodiments which incorporate the teachings of the present invention have been shown and described in detail herein, those skilled in the art can readily devise many other varied embodiments that still incorporate these teachings.

What is claimed is:

1. A method for disinfecting a sample of water, the method comprising:
   generating a current using an array of photovoltaic cells, wherein the array of photovoltaic cells encircles an exterior wall of a container holding the sample, wherein the array of photovoltaic cells comprises a plurality of micro photovoltaic cells, wherein the plurality of micro photovoltaic cells includes flexible thin-film photovoltaic cells;

powering an array of flexible light emitting diodes applied directly to an interior wall of the container holding the sample using the current that is generated, wherein the array of flexible light emitting diodes emits a germicidal wavelength of radiation, wherein the array of flexible light emitting diodes comprises a plurality of micro light emitting diodes, wherein the plurality of micro light emitting diodes includes flexible thin-film light emitting diodes, wherein the array of flexible light emitting diodes encircles the interior wall of the container, wherein the plurality of micro light emitting diodes comprises a plurality of spalled light emitting diodes, and wherein each light emitting diode of the plurality of spalled light emitting diodes is electrically coupled to other light emitting diodes of the plurality of spalled light emitting diodes via a system of interconnects; and exposing the sample of water to the radiation.

2. The method of claim 1, wherein the generating comprises:

exposing the array of photovoltaic cells to solar radiation, wherein the array of photovoltaic cells converts the solar radiation into the current.

3. The method of claim 1, wherein the current is in a milliwatt range.

4. The method of claim 1, wherein each light emitting diode in the plurality of micro light emitting diodes has dimensions of less than or equal to one hundred micrometers by one hundred micrometers.

5. The method of claim 1, wherein each light emitting in the plurality of micro light emitting diodes has a power output of approximately one milliwatt.

6. The method of claim 1, wherein the germicidal wavelength of radiation is an ultraviolet wavelength.

7. The method of claim 1, wherein the exposing continues for a length of time sufficient to sterilize a desired percentage of microorganisms contained in the sample of water.

8. The method of claim 1, wherein the exposing comprises:
placing the sample of water within the container; and
placing the container in a location exposed to solar radiation.

9. The method of claim 1, wherein the exposing results in a sterilization of at least one of: a bacterium, a mold, a yeast, a virus, or a protozoon in the sample of water.

10. A system for disinfecting a sample of water, the system comprising:

a container for holding the sample of water;

an array of photovoltaic cells coupled to the container for converting solar radiation into a current, wherein the array of photovoltaic cells encircles an exterior wall of the container, wherein the array of photovoltaic cells comprises a plurality of micro photovoltaic cells, wherein the plurality of micro photovoltaic cells includes flexible thin-film photovoltaic cells; and an array of flexible light emitting diodes coupled directly to an interior wall of the container and powered by the current, wherein the array of flexible light emitting diodes emits a germicidal wavelength of radiation, wherein the array of flexible light emitting diodes comprises a plurality of micro light emitting diodes, wherein the plurality of micro light emitting diodes includes flexible thin-film light emitting diodes, wherein the array of flexible light emitting diodes encircles the interior wall of the container, wherein the plurality of micro light emitting diodes comprises a plurality of spalled light emitting diodes, and wherein each light emitting diode of the plurality of spalled light emitting diodes is electrically coupled to other light emitting diodes of the plurality of spalled light emitting diodes via a system of interconnects.

11. The system of claim 10, wherein the current is in a milliwatt range.

12. The system of claim 10, wherein the plurality of micro photovoltaic cells is formed from at least one of: amorphous silicon, crystalline silicon, silicon germanium, germanium, indium gallium arsenide, or indium arsenide.

13. The system of claim 10, wherein each light emitting diode in the plurality of micro light emitting diodes has dimensions of less than or equal to one hundred micrometers by one hundred micrometers.

14. The system of claim 10, wherein the array of flexible light emitting diodes comprises a plurality of light emitting diodes formed from at least one of: aluminum gallium nitride or gallium nitride.

15. The system of claim 10, wherein each light emitting diode in the plurality of light emitting diodes has a power output of approximately one milliwatt.

16. The system of claim 10, wherein the germicidal wavelength of radiation is an ultraviolet wavelength.

17. The system of claim 10, wherein the container is formed from a Bisphenol A-free polymer.

18. A container for disinfecting a sample of water held by the container, the container comprising:

an array of photovoltaic cells encircling an exterior wall of the container, for converting solar radiation into a current, wherein the array of photovoltaic cells comprises a plurality of micro photovoltaic cells, wherein the plurality of micro photovoltaic cells includes flexible thin-film photovoltaic cells; and an array of flexible light emitting diodes directly applied to an interior wall of the container and powered by the current, wherein the array of flexible light emitting diodes emits a germicidal wavelength of radiation, wherein the array of flexible light emitting diodes comprises a plurality of micro light emitting diodes, wherein the plurality of micro light emitting diodes includes flexible thin-film light emitting diodes, wherein the array of flexible light emitting diodes encircles the interior wall of the container, wherein the plurality of micro light emitting diodes comprises a plurality of spalled light emitting diodes, and wherein each light emitting diode of the plurality of spalled light emitting diodes is electrically coupled to other light emitting diodes of the plurality of spalled light emitting diodes via a system of interconnects.

19. The method of claim 1, wherein the flexible thin-film photovoltaic cells are spalled photovoltaic cells.

20. The method of claim 1, wherein the plurality of spalled light emitting diodes is produced by bringing a patterned stamp into contact with a wafer upon which an array of light emitting diode structures is fabricated.

* * * * *